United States Patent
Vrba

(10) Patent No.: US 8,556,914 B2
(45) Date of Patent: Oct. 15, 2013

(54) MEDICAL DEVICE INCLUDING STRUCTURE FOR CROSSING AN OCCLUSION IN A VESSEL

(75) Inventor: Anthony C. Vrba, Maple Grove, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 734 days.

(21) Appl. No.: 11/611,738

(22) Filed: Dec. 15, 2006

(65) Prior Publication Data

US 2008/0147170 A1 Jun. 19, 2008

(51) Int. Cl.
*A61B 17/22* (2006.01)

(52) U.S. Cl.
USPC .......................................... 606/127; 606/159

(58) Field of Classification Search
USPC .................. 606/127, 159, 108; 604/164.13; 600/585; 138/118; D24/140
See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |

(Continued)

FOREIGN PATENT DOCUMENTS

| | | |
|---|---|---|
| AU | 723040 | 12/1997 |
| AU | 733966 | 4/1998 |

(Continued)

OTHER PUBLICATIONS

"Mechanical Design and Systems Handbook", H.A. Rothbart, 1964, p. 33-13 (one sheet).

*Primary Examiner* — Ryan Severson
*Assistant Examiner* — Tin Nguyen
(74) *Attorney, Agent, or Firm* — Seager, Tufte & Wickhem, LLC

(57) ABSTRACT

A medical device, such as a guidewire, catheter, or the like, that includes an elongated tubular member that includes a plurality of angled slots defined in at least a distal section thereof. The plurality of angled slots can form a generally spiral shaped pattern about the longitudinal axis of the tubular member, and can be useful, for example, in aiding a user of the device in crossing an occlusion in a vessel of a patient. In some embodiments, the distal section of the tubular member may have an outer diameter that is greater than the outer diameter of a proximal section of the tubular member. In some embodiments, a proximal section of the tubular member may include a plurality of slots defined therein, for example, that may be configured to increase the lateral flexibility of the tubular member.

30 Claims, 12 Drawing Sheets

(56) References Cited

U.S. PATENT DOCUMENTS

| | | |
|---|---|---|
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,030,503 A | 6/1977 | Clark, III |
| 4,142,119 A | 2/1979 | Madey |
| 4,215,703 A | 8/1980 | Wilson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,551,292 A | 11/1985 | Fletcher et al. |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,706,671 A | 11/1987 | Weinrib |
| 4,721,117 A | 1/1988 | Mar et al. |
| 4,737,153 A | 4/1988 | Shimamura et al. |
| 4,762,130 A | 8/1988 | Fogarty et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,817,613 A | 4/1989 | Jaraczewski et al. |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,863,442 A | 9/1989 | DeMello et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,979,951 A | 12/1990 | Simpson |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gamble |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,282,484 A | 2/1994 | Reger |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,354 A * | 5/1994 | Zacca et al. ................... 606/159 |
| 5,308,435 A | 5/1994 | Ruggles et al. |
| 5,315,906 A | 5/1994 | Ferenczi et al. |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,358,493 A | 10/1994 | Schweich et al. |
| 5,365,942 A | 11/1994 | Shank |
| 5,365,943 A | 11/1994 | Jansen |
| 5,366,464 A | 11/1994 | Belknap |
| 5,368,564 A | 11/1994 | Savage |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams |
| 5,423,799 A | 6/1995 | Shiu |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,460,187 A | 10/1995 | Daigle et al. |
| 5,470,330 A | 11/1995 | Goldenberg et al. |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,584,843 A | 12/1996 | Wulfman et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |

(56) References Cited

U.S. PATENT DOCUMENTS

| | | |
|---|---|---|
| 5,622,184 A | 4/1997 | Ashby et al. |
| 5,630,806 A | 5/1997 | Inagaki et al. |
| 5,637,089 A | 6/1997 | Abrams et al. |
| 5,656,011 A | 8/1997 | Uihlein et al. |
| 5,658,264 A | 8/1997 | Samson et al. |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,676,697 A | 10/1997 | McDonald |
| 5,682,894 A | 11/1997 | Orr et al. |
| 5,690,120 A | 11/1997 | Jacobsen et al. |
| 5,695,506 A | 12/1997 | Pike et al. |
| 5,707,350 A * | 1/1998 | Krause et al. .................. 604/22 |
| 5,720,300 A | 2/1998 | Fagan et al. |
| 5,720,749 A * | 2/1998 | Rupp ............................. 606/79 |
| 5,722,609 A | 3/1998 | Murakami |
| 5,728,063 A | 3/1998 | Preissman et al. |
| 5,738,742 A | 4/1998 | Stevens |
| 5,746,701 A | 5/1998 | Noone |
| 5,769,830 A | 6/1998 | Parker |
| 5,772,609 A | 6/1998 | Nguyen et al. |
| 5,779,721 A | 7/1998 | Nash |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,820,612 A | 10/1998 | Berg |
| 5,827,225 A | 10/1998 | Ma Schwab |
| 5,827,242 A | 10/1998 | Follmer et al. |
| 5,833,632 A | 11/1998 | Jacobsen et al. |
| 5,836,926 A | 11/1998 | Peterson et al. |
| 5,843,050 A | 12/1998 | Jones et al. |
| 5,843,244 A | 12/1998 | Pelton et al. |
| 5,851,203 A | 12/1998 | van Muiden |
| 5,895,378 A | 4/1999 | Nita |
| 5,897,537 A | 4/1999 | Berg et al. |
| 5,902,254 A | 5/1999 | Magram |
| 5,902,290 A | 5/1999 | Peacock, III et al. |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,954,651 A | 9/1999 | Berg et al. |
| 5,971,975 A | 10/1999 | Mills et al. |
| 5,972,019 A | 10/1999 | Engelson et al. |
| 6,001,068 A * | 12/1999 | Uchino et al. ................. 600/585 |
| 6,004,279 A | 12/1999 | Crowley et al. |
| 6,014,919 A | 1/2000 | Jacobsen et al. |
| 6,017,319 A | 1/2000 | Jacobsen et al. |
| 6,019,772 A | 2/2000 | Shefaram et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A | 3/2000 | Solar et al. |
| 6,045,547 A | 4/2000 | Ren et al. |
| 6,048,339 A | 4/2000 | Zirps et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,106,485 A | 8/2000 | McMahon |
| 6,106,488 A | 8/2000 | Fleming et al. |
| 6,139,510 A | 10/2000 | Palermo |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| 6,228,073 B1 | 5/2001 | Noone et al. |
| 6,235,042 B1 | 5/2001 | Katzman |
| 6,248,082 B1 | 6/2001 | Jafari |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,508,803 B1 | 1/2003 | Horikawa et al. |
| 6,524,301 B1 | 2/2003 | Wilson et al. |
| 6,530,934 B1 | 3/2003 | Jacobsen et al. |
| 6,547,779 B2 | 4/2003 | Levine et al. |
| 6,553,880 B2 | 4/2003 | Jacobsen et al. |
| 6,556,873 B1 | 4/2003 | Smits |
| 6,579,246 B2 * | 6/2003 | Jacobsen et al. .............. 600/585 |
| 6,591,472 B1 | 7/2003 | Noone et al. |
| 6,602,280 B2 | 8/2003 | Chobotov |
| 6,610,046 B1 | 8/2003 | Usami et al. |
| 6,623,448 B2 | 9/2003 | Slater |
| 6,636,758 B2 | 10/2003 | Sanchez et al. |
| 6,638,266 B2 | 10/2003 | Wilson et al. |
| 6,652,508 B2 | 11/2003 | Griffin et al. |
| 6,682,493 B2 | 1/2004 | Mirigian |
| 6,684,874 B2 | 2/2004 | Mizek et al. |
| 6,712,826 B2 | 3/2004 | Lui |
| 6,730,095 B2 | 5/2004 | Olson, Jr. et al. |
| 6,749,560 B1 | 6/2004 | Konstorum et al. |
| 6,766,720 B1 | 7/2004 | Jacobsen et al. |
| 6,777,644 B2 | 8/2004 | Peacock, III et al. |
| 6,811,544 B2 | 11/2004 | Schaer |
| 6,837,898 B2 | 1/2005 | Boyle et al. |
| 6,866,642 B2 | 3/2005 | Kellerman et al. |
| 6,875,949 B2 | 4/2005 | Hall |
| 6,887,235 B2 | 5/2005 | O'Connor et al. |
| 6,918,882 B2 | 7/2005 | Skujins et al. |
| 6,997,937 B2 | 2/2006 | Jacobsen et al. |
| 7,001,369 B2 | 2/2006 | Griffin et al. |
| 7,074,197 B2 | 7/2006 | Reynolds et al. |
| 2002/0019599 A1 | 2/2002 | Rooney et al. |
| 2003/0009208 A1 | 1/2003 | Snyder et al. |
| 2003/0060732 A1 | 3/2003 | Jacobsen et al. |
| 2003/0069522 A1 | 4/2003 | Jacobsen et al. |
| 2003/0139763 A1 | 7/2003 | Duerig et al. |
| 2004/0010194 A1 | 1/2004 | Kamiyama |
| 2004/0111044 A1 * | 6/2004 | Davis et al. .................... 600/585 |

(56) References Cited

U.S. PATENT DOCUMENTS

| | | | |
|---|---|---|---|
| 2004/0153110 A1* | 8/2004 | Kurz et al. | 606/159 |
| 2004/0167437 A1 | 8/2004 | Sharrow et al. | |
| 2004/0167441 A1 | 8/2004 | Reynolds et al. | |
| 2004/0181174 A2 | 9/2004 | Davis et al. | |
| 2004/0181176 A1 | 9/2004 | Jafari et al. | |
| 2004/0210163 A1* | 10/2004 | Osawa et al. | 600/585 |
| 2005/0065456 A1* | 3/2005 | Eskuri | 600/585 |
| 2006/0100687 A1 | 5/2006 | Fahey et al. | |
| 2006/0189896 A1 | 8/2006 | Davis et al. | |
| 2006/0264904 A1 | 11/2006 | Kerby et al. | |
| 2008/0021347 A1 | 1/2008 | Jacobsen et al. | |
| 2008/0021348 A1 | 1/2008 | Jacobsen et al. | |
| 2008/0021400 A1 | 1/2008 | Jacobsen et al. | |
| 2008/0021401 A1 | 1/2008 | Jacobsen et al. | |
| 2008/0021402 A1 | 1/2008 | Jacobsen et al. | |
| 2008/0021403 A1 | 1/2008 | Jacobsen et al. | |
| 2008/0021404 A1 | 1/2008 | Jacobsen et al. | |
| 2008/0021405 A1 | 1/2008 | Jacobsen et al. | |
| 2008/0021406 A1 | 1/2008 | Jacobsen et al. | |
| 2008/0021407 A1 | 1/2008 | Jacobsen et al. | |
| 2008/0021408 A1 | 1/2008 | Jacobsen et al. | |
| 2008/0077119 A1 | 3/2008 | Snyder et al. | |

FOREIGN PATENT DOCUMENTS

| | | |
|---|---|---|
| BR | PI 9712829 | 9/1997 |
| CA | 2266685 | 5/2006 |
| CN | 1230914 | 10/1999 |
| DE | 2539191 | 3/1976 |
| EP | 0 045 931 | 2/1982 |
| EP | 0 069 522 | 1/1983 |
| EP | 0 087 933 | 9/1983 |
| EP | 0 111 044 | 6/1984 |
| EP | 0 181 174 | 5/1986 |
| EP | 0377453 | 7/1990 |
| EP | 0 565 065 | 6/1996 |
| EP | 0 778 038 | 6/1997 |
| EP | 0 778 039 | 6/1997 |
| EP | 0 778 040 | 6/1997 |
| EP | 0 812 599 | 12/1997 |
| EP | 0 865 772 | 9/1998 |
| EP | 0 865 773 | 9/1998 |
| EP | 0 521 595 | 5/1999 |
| EP | 0 917 885 | 5/1999 |
| EP | 0 937 481 | 8/1999 |
| EP | 0 790 066 | 4/2000 |
| EP | 0 608 853 | 4/2003 |
| EP | 0 935 947 | 12/2004 |
| EP | 0 934 141 | 11/2005 |
| GB | 2214354 | 8/1989 |
| GB | 2257269 | 1/1993 |
| JP | 5-8522 | 1/1983 |
| JP | 60091858 | 5/1985 |
| JP | 61022752 | 1/1986 |
| JP | 62023361 | 1/1987 |
| JP | 62089470 | 4/1987 |
| JP | 62299277 | 12/1987 |
| JP | 6393516 | 4/1988 |
| JP | 63-181774 | 7/1988 |
| JP | 63217966 | 9/1988 |
| JP | 1089956 | 4/1989 |
| JP | 1135363 | 5/1989 |
| JP | 1158936 | 6/1989 |
| JP | 2107268 | 4/1990 |
| JP | 03-122850 | 12/1991 |
| JP | 4061840 | 2/1992 |
| JP | 4099963 | 3/1992 |
| JP | 4213069 | 8/1992 |
| JP | 4213070 | 8/1992 |
| JP | 4236965 | 8/1992 |
| JP | 5149969 | 6/1993 |
| JP | 5-506806 | 10/1993 |
| JP | 5-309159 | 11/1993 |
| JP | 5-507857 | 11/1993 |
| JP | 6-501179 | 2/1994 |
| JP | 631749 | 4/1994 |
| JP | 6169996 | 6/1994 |
| JP | 6-63224 | 9/1994 |
| JP | 6312313 | 11/1994 |
| JP | 728562 | 5/1995 |
| JP | 7124164 | 5/1995 |
| JP | 7124263 | 5/1995 |
| JP | 7136280 | 5/1995 |
| JP | 7148264 | 6/1995 |
| JP | 7505561 | 6/1995 |
| JP | 7037199 | 7/1995 |
| JP | 7185009 | 7/1995 |
| JP | 7255855 | 10/1995 |
| JP | 7275366 | 10/1995 |
| JP | 751067 | 11/1995 |
| JP | 8-229888 | 9/1996 |
| JP | 8509141 | 10/1996 |
| JP | 8317988 | 12/1996 |
| JP | 9000164 | 4/1997 |
| JP | 9-276413 | 10/1997 |
| JP | 9276413 | 10/1997 |
| JP | 9-294813 A | 11/1997 |
| JP | 9294813 | 11/1997 |
| JP | 10-118193 | 5/1998 |
| JP | 10-305039 | 11/1998 |
| JP | 10328191 | 12/1998 |
| JP | 11-226131 A | 8/1999 |
| JP | 11-267224 A | 10/1999 |
| JP | 3081831 | 6/2000 |
| JP | 2000197704 | 7/2000 |
| JP | 2000-510722 A | 8/2000 |
| JP | 2000-511083 A | 8/2000 |
| JP | 2001-500808 A | 1/2001 |
| JP | 2002-529137 A | 9/2002 |
| JP | 2002-542901 A | 12/2002 |
| JP | 2002-543896 A | 12/2002 |
| JP | 2003-517893 A | 6/2003 |
| JP | 2005-534407 | 11/2005 |
| SU | 712908 | 1/1980 |
| SU | 758421 | 8/1980 |
| SU | 1529365 | 12/1989 |
| WO | WO 90/02520 | 3/1990 |
| WO | WO 91/13364 | 9/1991 |
| WO | WO 92/04072 | 3/1992 |
| WO | WO 92/07619 | 5/1992 |
| WO | WO 93/04722 | 3/1993 |
| WO | WO 93/11313 | 6/1993 |
| WO | WO 95/24236 | 9/1995 |
| WO | WO 96/19255 | 6/1996 |
| WO | WO 97/10022 | 3/1997 |
| WO | WO 97/25914 | 7/1997 |
| WO | WO 97/43949 | 11/1997 |
| WO | WO 97/44083 | 11/1997 |
| WO | WO 97/44086 | 11/1997 |
| WO | WO 98/10694 | 3/1998 |
| WO | 9904847 | 2/1999 |
| WO | WO 99/11313 | 3/1999 |
| WO | WO 00/27303 | 5/2000 |
| WO | WO 00/30710 | 6/2000 |
| WO | WO 00/48645 | 8/2000 |
| WO | WO 00/57943 | 10/2000 |
| WO | WO 00/66199 | 11/2000 |
| WO | WO 00/67845 | 11/2000 |
| WO | WO 00/72907 | 12/2000 |
| WO | WO 01/28620 | 4/2001 |
| WO | 0136034 | 5/2001 |
| WO | 0145912 A1 | 6/2001 |
| WO | WO 01/45773 | 6/2001 |
| WO | WO 01/93920 | 12/2001 |
| WO | WO 02/13682 | 2/2002 |
| WO | WO 02/062540 | 8/2002 |
| WO | WO 03/004086 | 1/2003 |
| WO | WO 03/008148 | 1/2003 |
| WO | WO 2004/012804 | 2/2004 |
| WO | 2004047899 A1 | 6/2004 |

* cited by examiner

MEDICAL DEVICE INCLUDING STRUCTURE FOR CROSSING AN OCCLUSION IN A VESSEL

FIELD OF TECHNOLOGY

The invention relates generally to medical devices. More specifically, the invention relates to intracorporal medical devices, such as a guidewire, catheter, or the like, including structure for crossing an occlusion in a vessel of a patient.

BACKGROUND

The use of intravascular medical devices has become an effective method for treating many types of vascular disease. In general, one or more suitable intravascular device is inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular devices include percutaneous transluminal angioplasty (PTA) and percutaneous transluminal coronary angioplasty (PTCA).

When in use, intravascular devices, such as a guidewire, may enter the patient's vasculature at a convenient location and then is urged to a target region in the anatomy. The path taken within the anatomy of a patient may be very tortuous, and as such, it may be desirable to combine a number of performance features in the intravascular device. For example, it is sometimes desirable that the device have a relatively high level of pushability and torqueability, particularly near its proximal end. It is also sometimes desirable that a device be relatively flexible, particularly near its distal end, for example, to aid in steering.

In addition, medical devices, such as a guidewire, catheter, or the like, will sometimes confront an occlusion, such as a lesion and/or stenosis when passing through the vasculature to a target location. In some cases, the occlusion may completely block the vessel as is the case with a chronic total occlusion. The success of the procedure often depends on the ability to insert the medical device through the occlusion.

A number of different elongated medical device structures, assemblies, and methods are known, each having certain advantages and disadvantages. However, there is an ongoing need to provide alternative elongated medical device structures, assemblies, and methods. In particular, there is an ongoing need to provide alternative medical devices including structure or assemblies configured to aid in crossing an occlusion in a vessel of a patient, and methods of making and using such structures and/or assemblies.

SUMMARY OF SOME EMBODIMENTS

The invention provides several alternative designs, materials and methods of manufacturing and using alternative elongated medical device structures and assemblies. Some example embodiments relate to a medical device, such as a guidewire, catheter, or the like, that includes an elongated tubular member that includes a plurality of angled slots defined in at least a distal section thereof. The plurality of angled slots can form a generally spiral shaped pattern about the longitudinal axis of the tubular member, and can be useful, for example, in aiding a user of the device in crossing an occlusion in a vessel of a patient. For example, when an occlusion is engaged with the medical device, a rotational force may be applied such that the angled slots and/or one or more spiral shaped structure defined by the angled slots may engage the occlusion and may aid in pulling and/or drawing at least a portion of the medical device through the occlusion. In some embodiments, the distal section of the tubular member may have an outer diameter that is greater than the outer diameter of a proximal section of the tubular member. In some embodiments, a proximal section of the tubular member may include a plurality of slots defined therein, for example, that may be configured to increase the lateral flexibility of the tubular member. A number of alternative embodiments, including alternative structures and assemblies, and methods of making and using are also disclosed.

The above summary of some embodiments is not intended to describe each disclosed embodiment or every implementation of the present invention. The Figures, and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
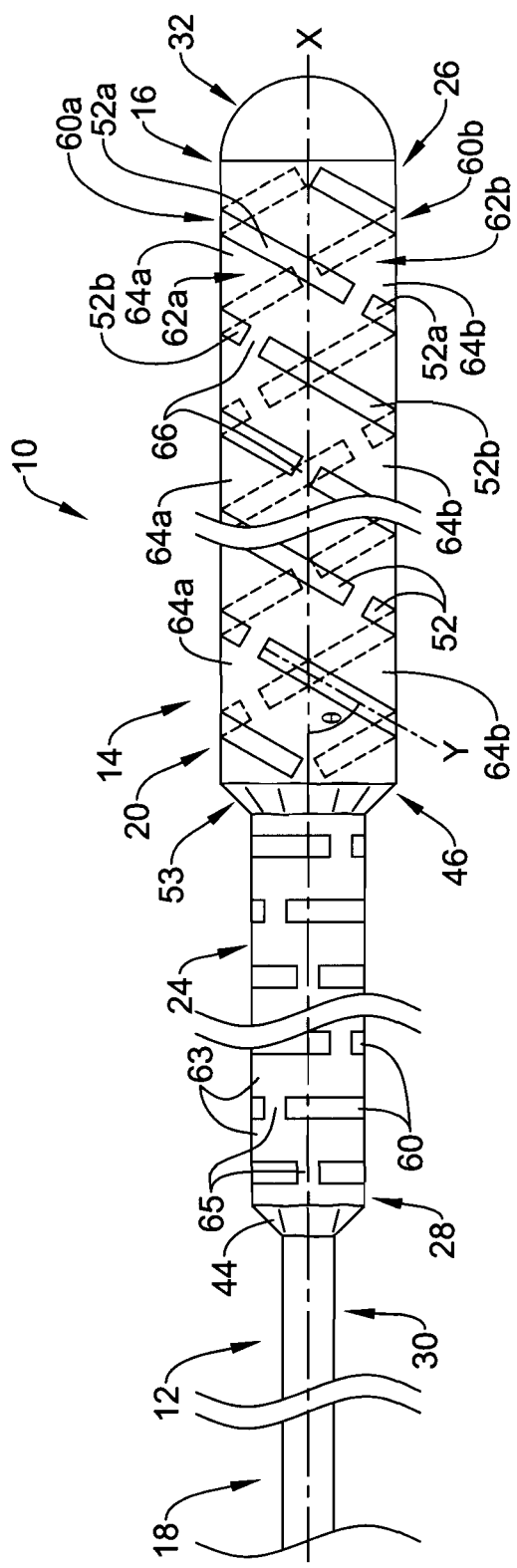
FIG. 1 is a partial side view of an example embodiment of a guidewire.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS OF THE INVENTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

As will be appreciated, at least some embodiments relate to a medical device that includes a tubular member having a plurality of angled slots defined in at least the distal section thereof, the angles slots forming a generally spiral shaped pattern about a portion of the tubular member. Such a tubular member may be used, for example, in the medical device to aid in crossing an occlusion in a vessel of a patient, as will be discussed in more detail below.

Refer now to FIG. 1 which illustrates a medical device 10 in accordance with one example embodiment. In the embodiment shown, the medical device 10 is in the form of a guidewire 10. Guidewire 10 can include a proximal region 12, a distal region 14, a distal end 16, and a proximal end 18. As used herein, the proximal region 12 and the distal region 14 may generically refer to any two adjacent guidewire sections along any portion of the guidewire 10. The guidewire 10 includes a generally tubular member 20 that includes a distal section 22, a proximal section 24, a distal end 26, and a proximal end 28. The tubular member 20 may extend longitudinally along a longitudinal axis X. Some additional aspects of the tubular member 20 will be discussed in more detail below.

The guidewire 10 may also include a core member 30 that may be attached to the tubular member 20, and extend from a location within the tubular member 20 and/or from the proximal end 28 of the tubular member 20 to the proximal end 18 of the guidewire 10. However, in other embodiments, the core member 30 may be absent, and/or the tubular member 20 may extend to the proximal end 18 of the guidewire 10. For example, in some other embodiments, the tubular member 20 may extend along substantially the entire length of the guidewire 10, for example, form the proximal end 18 to the distal end 16, and the core member 30 may be present and disposed within at least a portion of the tubular member 20, or may be absent, as desired. A distal tip member 32 may be disposed at the distal end 26 of the tubular member 20 and/or the distal end 16 of the guidewire 10. The distal tip member 32 may be any or a broad variety of suitable structures, for example, a solder tip, a weld tip, a pre-made or pre-formed metallic or polymer structure, or the like, that is attached or joined to the distal end of the tubular member 20 using a suitable attachment technique.

Figure 2:
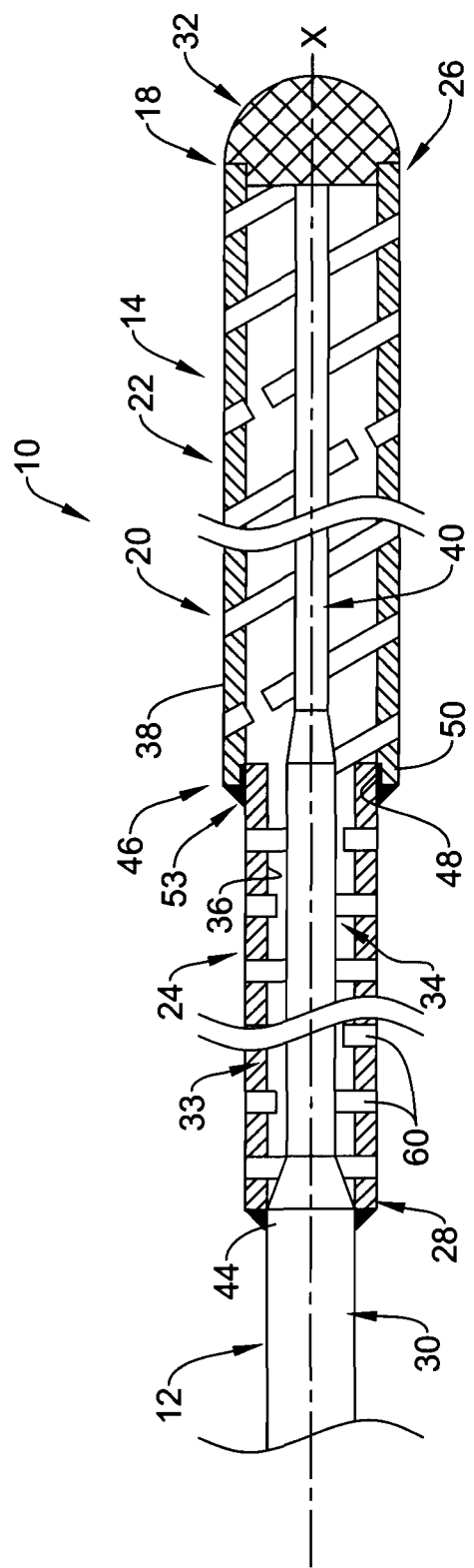
FIG. 2 is a partial cross-sectional view of the guidewire of FIG. 1.

Referring now to FIG. 2, the tubular member 20 includes a tubular wall 33 including an outer surface 38 and an inner surface 36 defining an inner lumen 34. As can be appreciated, a portion of the core member 30 may extend into at least a portion of the lumen 34. In the embodiment shown, the core member 30 includes a distal portion 40 that extends within the lumen 34, and a proximal portion 42 that extends proximally from the tubular member 20. The core member 30 can be attached to the tubular member 20 in any suitable manner and at any suitable location. For example, the core member 30 may be attached to the tubular member 20 through one or more attachment areas 44, which in this embodiment are disposed adjacent the proximal end 28 of the tubular member 20. It should be understood that additional attachment areas, and/or alternative positioning of attachment areas may be used in other embodiments. The core member 30 may also extend to, and be attached to the distal tip member 32. In other embodiments, however, the core member 30 may end proximally from the distal tip member and/or proximally of the distal end 26 of the tubular member 20. In addition, it should be understood that other structure or components, may be used in the guidewire construction, such as a shaping wire or ribbon, one or more coils, marker members, or the like, or others, some of which are discussed below.

As indicated above, the tubular member 20 includes both a distal section 22 and a proximal section 24. In some embodiments, tubular member 20 may be a single, continuous and/or uninterrupted and/or one-piece and/or monolithic tubular member that defines both the proximal and distal sections 22/24. In other embodiments, as shown in FIGS. 1 and 2, the tubular member 20 may include a plurality of discrete tubular components or sections that are attached to one another to form the tubular member 20, or portions thereof. For example, the distal section 22 and proximal section 24 may each be a discrete tubular component that are attached and/or secured to together to create the tubular member 20. The components may be attached using any suitable joining or bonding technique and/or structure. For example, the distal and proximal sections 22/24 may be joined using adhesive bonding, welding, soldering, brazing, mechanical bonding and/or fitting, or the like, or any other suitable technique. Additionally, the joint 46 may take the form of any suitable joint, such as a butt joint, an overlapping joint, or the like, and/or may include or incorporate other structure to form the joint. FIG. 2 shows an example of an overlapping type joint 46, wherein a portion of the distal end 48 of the proximal section 24 is disposed within, and overlaps with a portion of the proximal end 50 of the distal section 22. In forming the joint 46, or in a separate operation, a joining material or other filler material may be used to create transition structure 53 to provide a generally smooth or tapered transition between the distal and proximal sections 22/24, if desired. For example, a solder, brazing, welding, adhesive, polymer, or other material may be used in creating the transition structure 53. In embodiments, for example where the outer diameters of the distal and proximal sections 22/24 are different, the transition structure 53 may form a ramp like structure. A similar arrangement may be used, for example, at the attachment area 44, where the proximal end of the tubular member 20 is attached to the core member 30, for example, if the core member 30 has a smaller outer diameter than the proximal section 24 of the tubular member 20.

As can also be appreciated, in some embodiments, the distal section 22, or portions thereof, can have an outer diameter that is greater than the outer diameter of the proximal section 24. In some embodiments, this may provide for certain benefits. For example, the distal section 22, due to its greater diameter, may be better adapted to engage an occlusion in a vessel of a patient, as will be discussed below. Additionally, the proximal section 24, due to its reduced diameter relative to the distal section 22, may extend through a pathway in an occlusion created by the larger distal section 22 with a reduced amount of drag and/or engagement with the occlusion and/or other parts of the vessel. Additionally, the proximal section, due to its reduced diameter, may also be provided with greater flexibility relative to the distal section 22. These are but of few examples of some benefits that may be realized due to the distal section 22 including a greater outer diameter than the proximal section 24 of the tubular member 22. In other embodiments, however, the outer diameter of the distal section 22, or portions thereof, may be the same or smaller than the outer diameter of the proximal section, as will be discussed in more detail below. In embodiments where the distal and proximal sections 22/24 are two discrete and/or separate components that are attached, the variances in the outer diameters can be provided by the use of different discrete tubular components having different outer diameters. In embodiments where the tubular member 20 is a one-piece or monolithic member, the variances in the outer diameters can be provided by grinding or otherwise working the tubular member 20 to provide the desired diameters.

The distal section 22 includes a plurality of angled cuts, apertures, and/or slots 52 defined in the wall 33. This plurality of angled slots 52 can be disposed such that they form one or more generally spiral-shaped pattern in the distal section 22 of the tubular member 20 about the longitudinal axis x. In other words, the slots 52 can be disposed and/or created such that they are at an angle relative to the longitudinal axis x, and a plurality of the angled slots 52 in combination may form a generally spiral-shaped pattern about the longitudinal axis x. For example, the slots 52 may include a center line y that extends both laterally along and radially about the longitudinal axis x. The center line y may lie in a plane that can define an angle $\Theta$ with the longitudinal axis x, and the angle $\Theta$ is generally less than about 90°. In some embodiments, the angle $\Theta$ may be in the range of about 35° to 85°, or from about 40° to 80°, or from about 45° to 75°, or from about 50° to 70°. In some cases, the angle $\Theta$ may be about 50°, about 60°, about 70°, or about 80°. In some embodiments, at least some, if not all of the slots 52 are disposed at the same or a similar angle. However, in other embodiments, one or more slots 52 may be disposed at different angles relative to other slots 52. Because the slots 52 are angled relative to the longitudinal axis x, and the outer surface of the tubular member 20 is curved, the slots 52 can take a curved, and/or spiral-like shape about a portion of the outer surface of the tubular member 20. As such, a plurality of the slots 52 may be used to create one or more generally spiral-shaped pattern about the outer surface of the tubular member 20.

In some embodiments, each individual slot 52 extends only partially in a radial manner about the longitudinal axis x. In other words, each slot 52 makes less than one full revolution about the longitudinal axis x. For example, FIG. 1 shows portions of slots 52 in phantom where they extend radially to the opposite side of the tubular member 20—and as can be appreciated, in this embodiment, the slots 42 do not extend fully about the longitudinal axis x of the tubular member 20. Such arrangements may allow for certain benefits, such as enhanced torque transmission. However, in other embodiments, one or more slots 52 may extend for a full revolution or more radially about the longitudinal axis x, as desired. In some embodiments, at least some if not all of the slots 52 may extend all the way through the wall 33 of the tubular member 22, such that there is fluid communication between the lumen 34 and the exterior of the tube 20. In other embodiments, however, some or all of the slots 52 may extend only partially into the wall 33, such that the slots 52 may be more channel-like structures in the outer surface of the tubular member 20.

The shape and size of the slots 52 can vary, for example, to achieve the desired characteristics. For example, the shape of slots 52 can vary to include essentially any appropriate shape, such as rectangular, pill-shaped, oval, or the like, and may include rounded or squared edges, and can be variable in length and width, and the like.

In some embodiments, a spiral shaped pattern can be formed by aligning and/or arranging at least some of the slots 52 in combination such that they form what may be characterized as a generally non-continuous spiral groove that extends radially about the outer surface of the distal section 22. For example, with reference to FIG. 1, slots 52*a* may be arranged in a generally end-to-end manner with each other, such that two or more slots 52*a* in combination form a spiral-shaped, cork-screw like, and/or thread-like non-continuous spiral groove 60*a* about the outer surface of the tubular member 20. As can be appreciated, because the slots 52*a* are not connected, the spiral groove 60*a* created is generally non-continuous. Additional slots 52 can be added to continue the pattern. The embodiment shown also includes a second generally non-continuous spiral groove 60*b* including slots 52*b*. In other embodiments, only one, or more than two such non-continuous spiral grooves may be defined to create a generally spiral shaped pattern.

The generally spiral-shaped pattern shown in FIG. 1 may also be described in terms of at least some of the structure that remains after the slots 52 are formed and/or created in the distal section 22. For example, once the slots 52 are created, at least some of the remaining portions in the distal section 22 can define and/or include one or more structures that may be spiral-like in shape. In some cases, the remaining portions of the distal section 22 may take the shape of one or more spiral-like structure including a plurality of rings and/or turns that are interconnected by lateral beams. In FIG. 1, two generally spiral like structures 62*a* and 62*b* are shown—at least partially defined by and/or defining the two generally non-continuous spiral grooves 60*a* and 60*b*. Spiral like structure 62*a* includes a plurality of rings and/or turns 64*a*, and spiral like structure 62*b* includes a plurality of rings and/or turns 64*b*. The rings and/or turns 64*a*/64*b* may be interconnected by beams 66. In other embodiments, only one such spiral-like structure may be defined, for example, where only one non-continuous spiral groove is defined, and each ring and/or turn of such a structure may be interconnected by one or more beams. In yet other embodiments, more than two such spiral-like structures may be defined, for example, where more than two non-continuous spiral grooves are defined. Again, the rings and/or turns of the structure may be interconnected by beams. Such structures may be characterized, for example, as spiraled connected ring structures.

The embodiment shown in FIG. 1, however, is just one example embodiment of a generally spiral-shaped pattern that may be created with angled slots. For example, in some embodiments, at least some of the angled slots may not be disposed in direct end-to-end alignment, but may be somewhat or completely offset from one another.

Figure 1A:
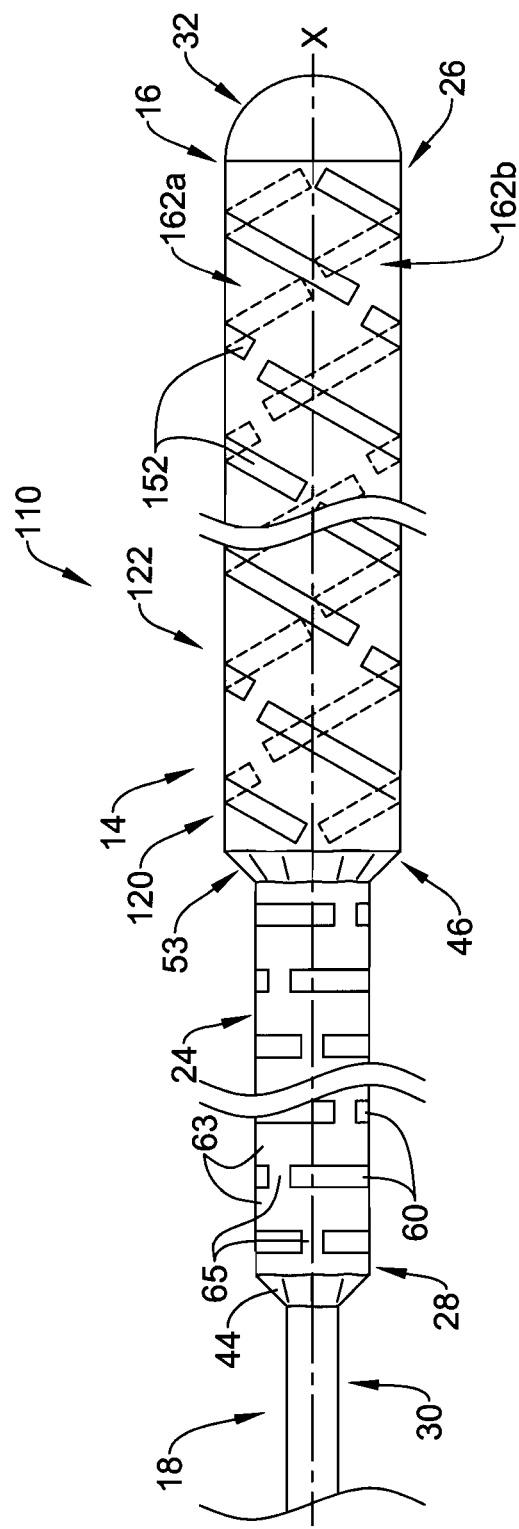
FIG. 1A is a partial side view of another example embodiment of a guidewire similar to that shown in FIG. 1, but including a different pattern of slots formed in the distal section.
Figure 1B:
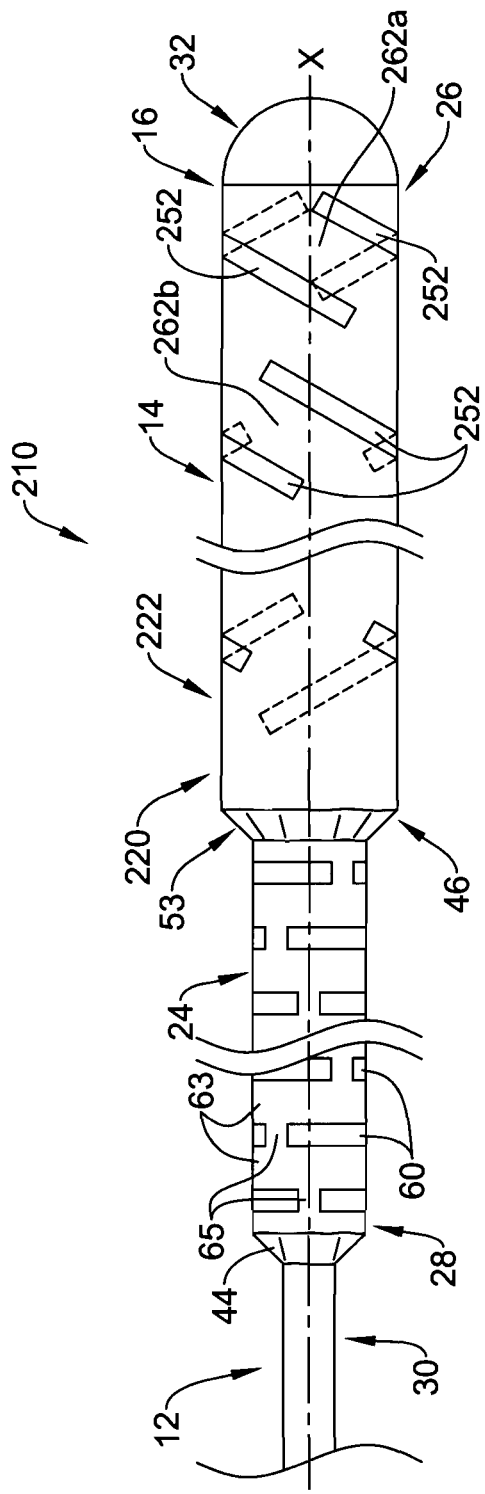
FIG. 1B is a partial side view of another example embodiment of a guidewire similar to that shown in FIG. 1, but including a different pattern of slots formed in the distal section.

For example, refer to FIG. 1A which shows a guidewire 110 similar to that shown in FIG. 1, wherein like reference numbers indicates similar structure. In the embodiment of FIG. 1, the angled slots 152 are disposed in a pattern such that they are somewhat offset from direct end-to-end alignment, but the pattern of slots 152 and/or remaining structures 162*a* and 162*b* may still be characterized as generally spiral-shaped and/or spiral like. In other embodiments, slots may not be disposed in any type of end-to-end arrangement, or may be separated by greater distances, but may still form a generally spiral-shaped pattern. For example, refer to FIG. 1B which shows another alternative guidewire 210 similar to that shown in FIG. 1, wherein like reference numbers indicates similar structure. The pattern of slots 252 that may be used on the distal section 222 of a tubular member 220 are not necessarily in any end-to-end relationship, but the pattern of slots 252 and/or at least some of the remaining structures 262a and 262b may still be characterized as generally spiral-shaped and/or spiral like. A broad variety of other generally spiral-shaped patterns is contemplated and may be achieved using angled slots 52 in a distal section 22 of a tubular member 20.

In at least some embodiments, the spiral-shaped pattern of slots 52 and/or spiral-shaped remaining structure in the distal section 22 may be configured to aid a user to cross an occlusion in a vessel of a patient. For example, the distal section 22, including such a spiral-shaped pattern of slots and/or spiral-shaped remaining structure, may be configured to function as a screw-like, auger-like, and/or threaded member that may engage the occlusion and draw itself and/or a portion of the guidewire 10 into and/or through the occlusion when a predetermined rotational force is applied to the guidewire. Some examples of such uses are discussed below. Additionally, the slots 52 can be disposed in a pattern that provides the desired degree of lateral flexibility while maintaining a desired degree of tortional stiffness.

Referring back to FIG. 1, the proximal section 24, or portions thereof, may also include a plurality of slots 60 formed in at least a portion thereof. For example, slots 60 may be provided to enhance the flexibility of the tubular member 20, while still allowing for suitable torque transmission characteristics. In some embodiments, at least some of the slots 60 can be disposed at an angle relative to the longitudinal axis x that is different from the angle of the slots 52, but in some cases they may be the same. In some embodiments, the slots 60 may be disposed at an angle that is generally perpendicular to the longitudinal axis x. Similar to as suggested above, the apertures 60 may be formed such that one or more rings and/or turns 63 interconnected by one or more beams 65 are formed in the tubular member 20, and such rings 63 and beams 65 may include portions of the tubular member 20 that remain after the slots 60 are formed in the body of the tubular member 20. Such an interconnected ring structure may act to maintain a relatively high degree of tortional stiffness, while maintaining a desired level of lateral flexibility. In some embodiments, some adjacent slots 60 can be formed such that they include portions that overlap with each other about the circumference of the tube 20. In other embodiments, some adjacent slots 60 can be disposed such that they do not necessarily overlap with each other, but are disposed in a pattern that provides the desired degree of lateral flexibility. Additionally, the slots 60 can be arranged along the length of, or about the circumference of, the tubular member 20 to achieve desired properties. For example, the slots 60 can be arranged in a symmetrical pattern, such as being disposed essentially equally on opposite sides about the circumference of the tubular member 20, or equally spaced along the length of the proximal section 24 of the tubular member 20, or can be arranged in an increasing or decreasing density pattern, or can be arranged in a non-symmetric or irregular pattern. In other embodiments, however, it is contemplated that the proximal section may not include any such slots 60.

Any of the above mentioned slots, for example slots 52 or 60, can be formed in essentially any known way. For example, slots 52 or 60 can be formed by methods such as micro-machining, saw-cutting, laser cutting, grinding, milling, casting, molding, chemically etching or treating, or other known methods, and the like. In some such embodiments, the structure of the tubular member 20 is formed by cutting and/or removing portions of the tube to form slots 52/60. Some example embodiments of appropriate micromachining methods and other cutting methods, and structures for tubular members and medical devices including tubular members are disclosed in U.S. Patent Publication No. U.S. 2003/0069522 entitled "Slotted Medical Device" filed Aug. 5, 2002; U.S. Patent Publication No. 2004/0181174-A2 entitled "Medical device for navigation through anatomy and method of making same" filed on Jul. 25, 2003; U.S. Pat. No. 6,766,720; and U.S. Pat. No. 6,579,246, the entire disclosures of which are herein incorporated by reference. Some example embodiments of etching processes are described in U.S. Pat. No. 5,106,455, the entire disclosure of which is herein incorporated by reference.

Forming the tubular member 20, or sections thereof, may include any one of a number of different techniques. For example, the tubular member 20, including the distal and proximal sections 22/24 and/or components, may be created by casting or forming methods, stamping methods, or the like, and may be shaped or otherwise worked, for example, by centerless grinding methods, into the desired shape and/or form. A centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing tubular member 20 during the grinding process. In some embodiments, tubular member 20 is centerless ground using a Royal Master HI-AC centerless grinder.

Figure 3:
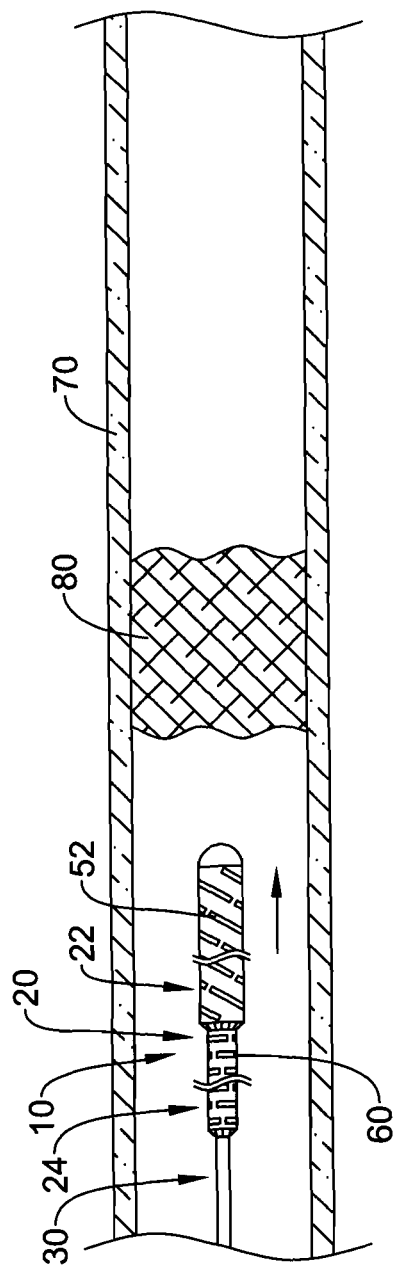
FIG. 3 is a partial cross-sectional view of a vessel of a patient including an occlusion disposed therein with the guidewire of FIG. 1 disposed within the vessel and being advanced toward the obstruction.
Figure 4:
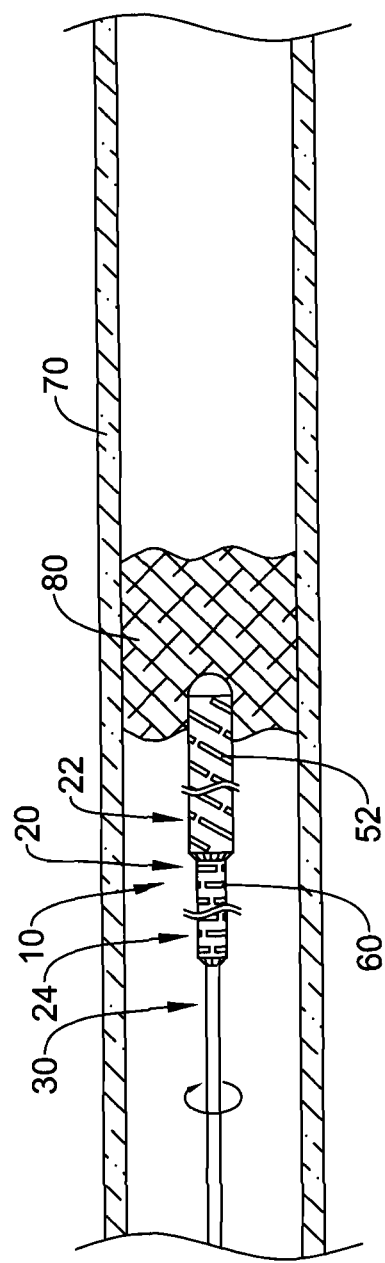
FIG. 4 is a view similar to that shown in FIG. 3, but with the distal section of the guidewire engaging the obstruction and being rotated to advance into the obstruction.
Figure 5:
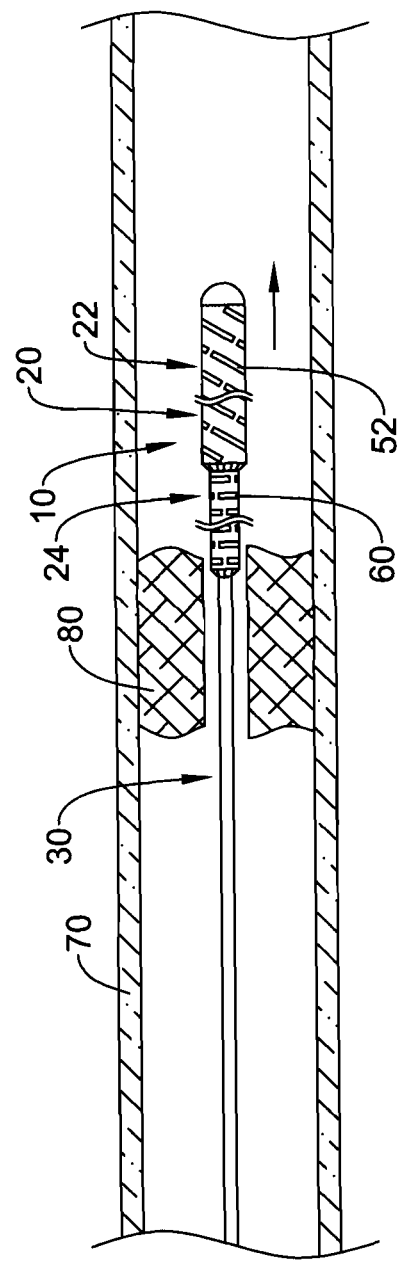
FIG. 5 is a view similar to that shown in FIG. 3, but showing the guidewire extending through the obstruction.

Refer now to FIGS. 3, 4, and 5 which may be used in providing a discussion of one example of use of the guidewire 10. As mentioned above, the guidewire 10 may be configured to aid a user to cross an occlusion in a vessel of a patient. In particular, the spiral-shaped pattern of slots 52 and/or spiral-shaped remaining structure in the distal section 22 of the guidewire 10 may be configured to aid in drawing and/or pulling the guidewire 10 into and/or through an occlusion. As shown in FIG. 4, the guidewire 10 may be advanced through the patient's vasculature, for example in a vessel 70, until it reaches an occlusion 80 within the vessel 70. As shown in FIG. 5, the distal section 22 of the guidewire 10 may be forced to contact the occlusion 80, for example, may be pushed slightly into the occlusion 80. The guidewire 10 may be rotated such that at least part of the spiral-shaped pattern of slots 52 and/or spiral-shaped remaining structure in the distal section 22 engages a portion of the occlusion 80. As the guidewire 10 is rotated in a predetermined direction, the spiral-shaped pattern of slots 52 and/or spiral-shaped remaining structure in the distal section 22 can engage the occlusion in a screw-like, auger-like, and/or threaded-like manner and draw and/or pull the guidewire 10 into the occlusion 80. Continued application of rotational force, in some cases in combination with lateral force, may allow the distal section to continue to screw and/or auger into the occlusion, and ultimately pass through the occlusion, as shown in FIG. 5. Once the guidewire 10 is passed through the occlusion, another device, such as a catheter, atherectomy device, distal protection device, or the like may be threaded onto the guidewire and urged distally and passed through the occlusion and/or may be used to treat the occlusion.

The materials that can be used for the various components of guidewire 10 may include those commonly associated with medical devices. For example, core member 30 and/or tubular member 20 may be made from a metal, metal alloy, a metal-polymer composite, and the like, or any other suitable material. Some examples of suitable metals and metal alloys include stainless steel, such as 304V, 304L, and 316LV stainless steel; mild steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 625, or the like; other Co—Cr alloys; platinum enriched stainless steel; or other suitable material.

As alluded to above, within the family of commercially available nickel-titanium or nitinol alloys, is a category designated "linear elastic" which, although it may be similar in chemistry to conventional shape memory and superelastic varieties, exhibits distinct and useful mechanical properties. By the applications of cold work, directional stress, and heat treatment, the material is fabricated in such a way that it does not display a substantial "superelastic plateau" or "flag region" in its stress/strain curve. Instead, as recoverable strain increases, the stress continues to increase in a generally linear relationship (as compared to that of super-elastic material, which has a super-elastic plateau) until plastic deformation begins. In some embodiments, the linear elastic nickel-titanium alloy is an alloy that does not show any substantial martensite/austenite phase changes that are detectable by DSC and DMTA analysis over a large temperature range.

For example, in some embodiments, there are no substantial martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy. Accordingly, components of guidewire 10 such as core member 30 and/or tubular member 20 may include linear elastic nickel-titanium alloy.

In some embodiments, the linear elastic nickel-titanium alloy is in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. In some other embodiments, a superelastic alloy, for example a superelastic nitinol can be used to achieve desired properties.

In at least some embodiments, portions or all of core member 30 and/or tubular member 20, or other components that are part of or used in the device, may be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of guidewire 10 to achieve the same result.

In some embodiments, a degree of MRI compatibility is imparted into device 10. For example, to enhance compatibility with Magnetic Resonance Imaging (MRI) machines, it may be desirable to make core member 30 and/or tubular member 20, or other portions of the medical device 10, in a manner that would impart a degree of MRI compatibility. For example, core member 30 and/or tubular member 20, or portions thereof, may be made of a material that does not substantially distort the image and create substantial artifacts (artifacts are gaps in the image). Certain ferromagnetic materials, for example, may not be suitable because they may create artifacts in an MRI image. Core member 30 and/or tubular member 20, or portions thereof, may also be made from a material that the MRI machine can image. Some materials that exhibit these characteristics include, for example, tungsten, Elgiloy, MP35N, nitinol, and the like, and others.

Referring now to core member 30, the entire core member 30 can be made of the same material along its length, or in some embodiments, can include portions or sections made of different materials. In some embodiments, the material used to construct core member 30 is chosen to impart varying flexibility and stiffness characteristics to different portions of core member 30. For example, the proximal region and the distal region of core wire 30 may be formed of different materials, for example materials having different moduli of elasticity, resulting in a difference in flexibility. In some embodiments, the material used to construct the proximal region can be relatively stiff for pushability and torqueability, and the material used to construct the distal region can be relatively flexible by comparison for better lateral trackability and steerability. For example, the proximal region can be formed of straightened 304v stainless steel wire or ribbon and the distal region can be formed of a straightened super elastic or linear elastic alloy, for example a nickel-titanium alloy wire or ribbon.

In embodiments where different portions of core member 30 are made of different materials, the different portions can be connected using any suitable connecting techniques. For example, the different portions of core member 30 can be connected using welding (including laser welding), soldering, brazing, adhesive, or the like, or combinations thereof. Additionally, some embodiments can include one or more mechanical connectors or connector assemblies to connect the different portions of core member 30 that are made of different materials. The connector may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Some other examples of suitable techniques and structures that can be used to interconnect different shaft sections are disclosed in U.S. Pat. Nos. 6,918,882 and 7,074,197, and U.S. Publication No. 2004/0167441 entitled "Composite Medical Device" filed on Feb. 26, 2003, all of which are incorporated herein by reference in their entirety.

Core member 30 can have a solid cross-section, for example a core wire, but in some embodiments, can have a hollow cross-section. In yet other embodiments, core member 30 can include a combination of areas having solid cross-sections and hollow cross sections. Moreover, core member 30, or portions thereof, can be made of rounded wire, flattened ribbon, or other such structures having various cross-sectional geometries. The cross-sectional geometries along the length of core member 30 can also be constant or can vary. For example, FIG. 2 depicts core member 30 as having a round cross-sectional shape. It can be appreciated that other cross-sectional shapes or combinations of shapes may be utilized without departing from the spirit of the invention. For example, the cross-sectional shape of core member 30 may be oval, rectangular, square, polygonal, and the like, or any suitable shape. Additionally, the core member 30 may include one or more tapered portions, for example, to provide for desired flexibility characteristics. Such tapers can be made or exist in a linear, stepwise, curvilinear, or other suitable fashion to achieve the desired results. For example, in the embodiment shown in FIG. 2, the core member 30 includes a plurality of tapered sections and constant diameter section.

In some embodiments, a sheath and/or coating, for example a lubricious, a hydrophilic, a protective, or other type of material may be applied over portions or all of the core member 30 and/or tubular member 20, or other portions of device 10. Some examples of suitable polymer sheath materials may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In some embodiments sheath material can be blended with a liquid crystal polymer (LCP). For example, the mixture can contain up to about 6% LCP. This has been found to enhance torqueability. By employing selection of materials and processing techniques, thermoplastic, solvent soluble, and thermosetting variants of these and other materials can be employed to achieve the desired results. Some examples of suitable coating materials may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Some coating polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

A coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

The length of the guidewire 10 is typically dictated by the length and flexibility characteristics desired in the final medical device. For example, proximal section 12 may have a length in the range of about 20 to about 300 centimeters or more, the distal section 14 may have a length in the range of about 3 to about 50 centimeters or more, and the medical device 10 may have a total length in the range of about 25 to about 350 centimeters or more. It can be appreciated that alterations in the length of sections and/or of the guidewire 10 as a whole can be made without departing from the spirit of the invention.

It should also be understood that a broad variety of other structures and/or components may be used in the guidewire construction. Some examples of other structures that may be used in the guidewire 10 include one or more coil members, braids, shaping or safety structures, such as a shaping ribbon or wire, marker members, such as marker bands or coils, centering structures for centering the core wire within the tubular member, such as a centering ring, an extension system, for example, to effectively lengthen the guidewire for aiding in exchanging other devices, or the like, or other structures. Those of skill in the art and others will recognize that the materials, structure, and dimensions of the guidewire may be dictated primary by the desired characteristics and function of the final guidewire, and that any of a broad range of materials, structures, and dimensions can be used.

Figure 6:
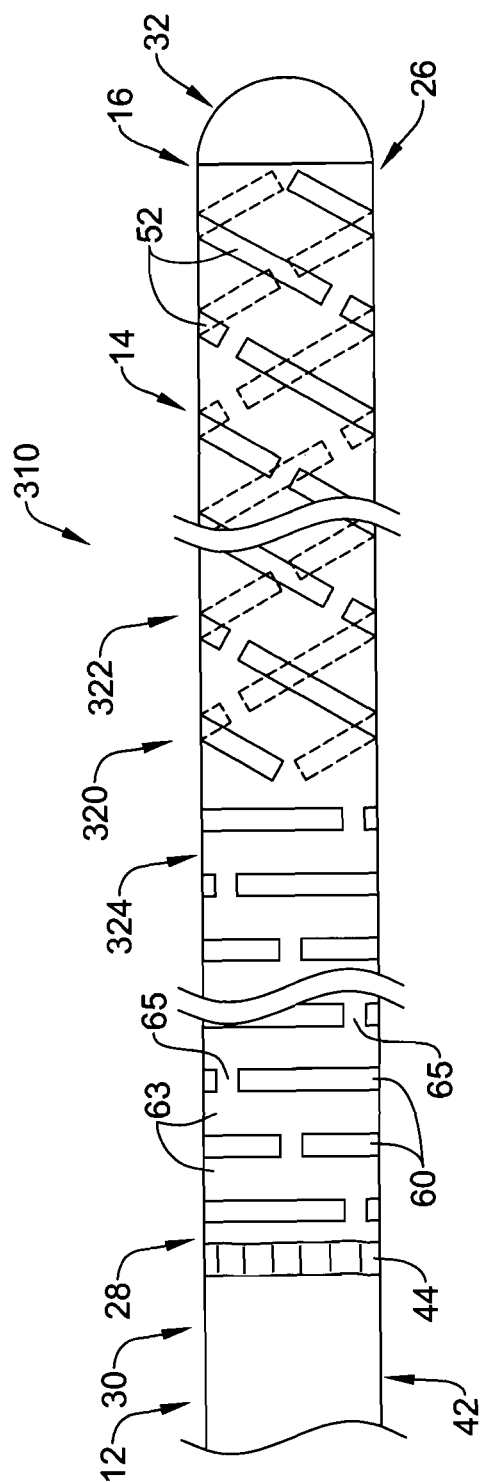
FIG. 6 is a partial side view of another example embodiment of a guidewire.
Figure 7:
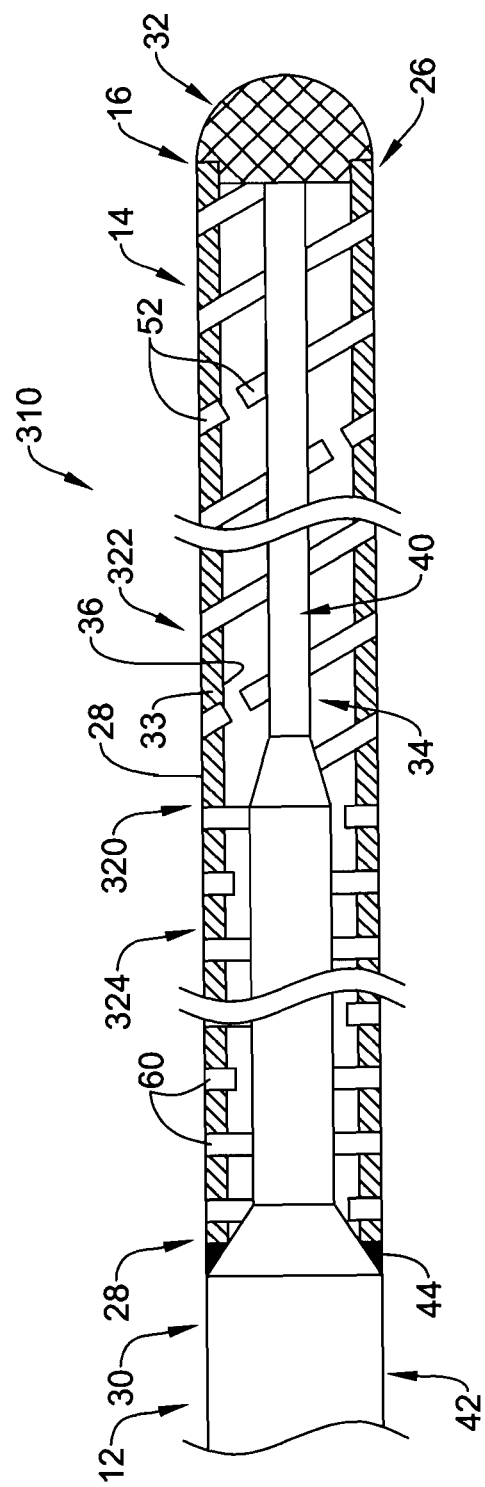
FIG. 7 is a partial cross-sectional view of the guidewire of FIG. 6.

Refer now to FIGS. 6 and 7, which show another alternative embodiment of a guidewire 310 which may include some similarities to the guidewire 10, wherein common reference numbers indicate similar structure. In this embodiment, however, the generally tubular member 320 is a single, continuous and/or uninterrupted and/or one-piece and/or monolithic tubular member that defines both the proximal and distal sections 322/324, and therefore does not include a joint, such as joint 46 in the embodiment of FIGS. 1 and 2. Additionally, as can be appreciated, in this embodiment, the proximal and distal sections 322/324 have generally the same outer diameter, and the proximal section 324 has generally the same outer diameter as the proximal section 42 of the core member 30. Again, the distal section 322 of the tubular member 322 includes a plurality of angled slots 52 disposed therein that may form a generally spiral-shaped pattern, for example, in a manner as discussed above. Again, such a guidewire 310 may be used in a similar manner as guidewire 10 as discussed above, for example, in the crossing of an occlusion in a vessel.

Figure 8:
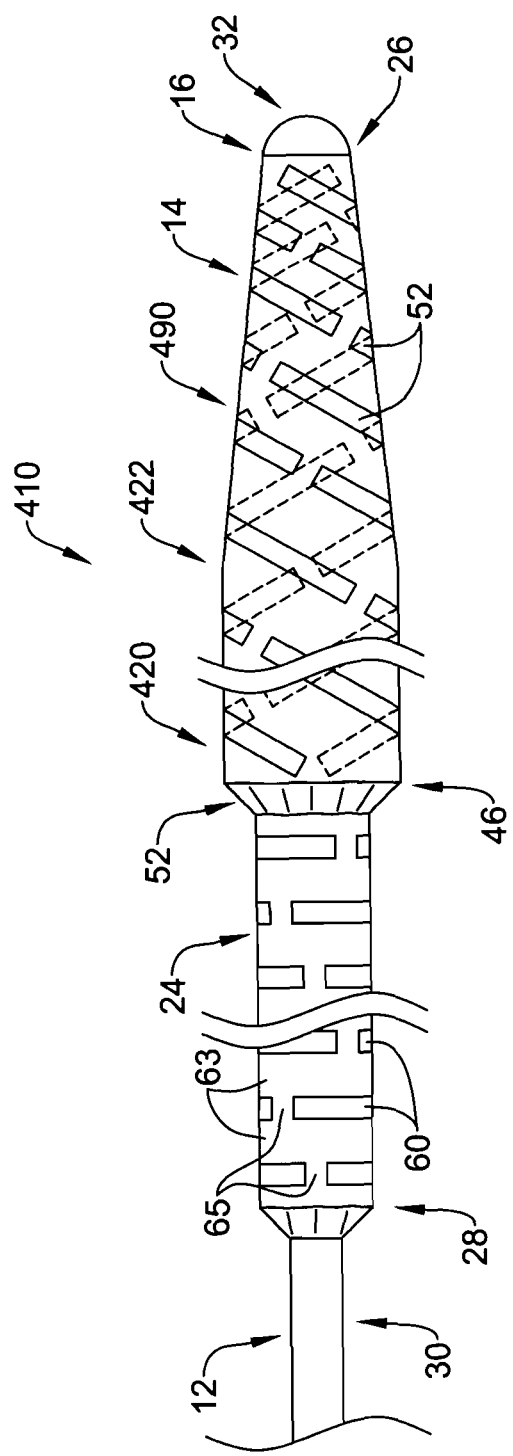
FIG. 8 is a partial side view of another example embodiment of a guidewire.

Refer now to FIG. 8, which shows another alternative embodiment of a guidewire 410 which may include some similarities to the guidewires discussed above, wherein common reference numbers indicate similar structure. In this embodiment, however, the distal section 422 of the tubular member 420 may be tapered. For example, the distal section may include one or more tapered regions 490 that can taper distally such that the outer diameter of the distal section 422 is reduced. Such tapering may occur in a generally linear manner, as shown, or may be tapered in a curvilinear fashion, and/or may include a plurality of stepwise tapers. Such tapering may be configured to aid in allowing the device to engage an occlusion. Again, the distal section 422 includes a plurality of angled slots 52 disposed therein that may form a generally spiral-shaped pattern, for example, in a manner as discussed above, and the guidewire 410 may be used in a similar manner as guidewire 10 as discussed above, for example, in the crossing of an occlusion in a vessel.

Figure 9:
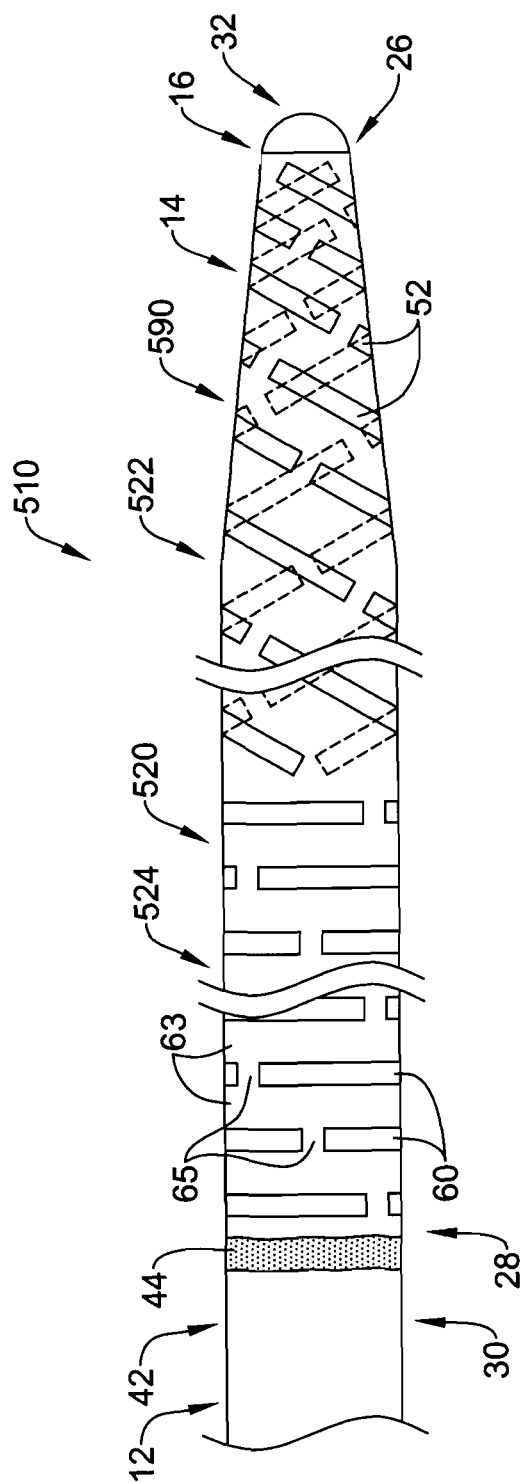
FIG. 9 is a partial side view of another example embodiment of a guidewire.

Refer now to FIG. 9, which show another alternative embodiment of a guidewire 510 which may include some similarities to some of the guidewires shown above, wherein common reference numbers indicate similar structure. Similar to the embodiment shown in FIGS. 6 and 7, in this embodiment, the generally tubular member 520 is a single, continuous and/or uninterrupted and/or one-piece and/or monolithic tubular member that defines both the proximal and distal sections 524/522, and therefore does not include a joint, such as joint 46 in the embodiment of FIGS. 1 and 2. Additionally, as can be appreciated, the outer diameter of the distal section 522 is not larger than the outer diameter of the proximal section 524. In fact, the distal section 522 may be tapered, for example, similar to that shown in FIG. 8. For example, the distal section 522 may include one or more tapered regions 590 that can taper distally such that the outer diameter of the distal section 422 is reduced. Again, the distal section 522 may include a plurality of angled slots 52 disposed therein that may form a generally spiral-shaped pattern, for example, in a manner as discussed above, and the guidewire 510 may be used in a similar manner as guidewire 10 as discussed above, for example, in the crossing of an occlusion in a vessel.

Figure 10:
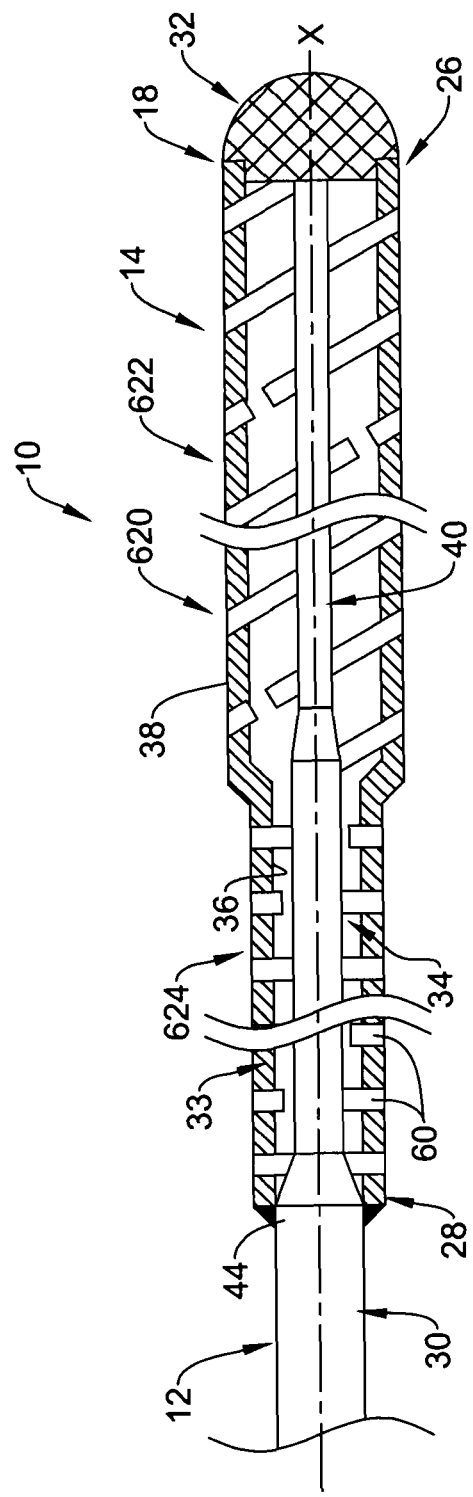
FIG. 10 is a partial cross-sectional view of another example embodiment of a guidewire.

Refer now to FIG. 10, which shows another alternative embodiment of a guidewire 610 which may include some similarities to the guidewire 10, wherein common reference numbers indicate similar structure. In this embodiment, however, the generally tubular member 620 is a single, continuous and/or uninterrupted and/or one-piece and/or monolithic tubular member that defines both the proximal and distal sections 624/622, and therefore does not include a joint, such as joint 46 in the embodiment of FIGS. 1 and 2. Additionally, as can be appreciated, in this embodiment, the distal section 622 has a larger outer diameter than the proximal section 624. Again, the distal section 622 of the tubular member 620 includes a plurality of angled slots 52 disposed therein that may form a generally spiral-shaped pattern, for example, in a manner as discussed above. Again, such a guidewire 610 may be used in a similar manner as guidewire 10 as discussed above, for example, in the crossing of an occlusion in a vessel.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. For example, although set forth with specific reference to guidewires in some of the example embodiments shown in the Figures and discussed above, the invention may relate to virtually any medical device including an elongate tubular member having a distal section including a plurality of angled slots defined therein that form a generally spiral shaped pattern about the longitudinal axis. Such structure may aid a user of the device in crossing an occlusion in a blood. For example, the invention may be applied to medical devices such as a balloon catheter, an atherectomy catheter, a drug delivery catheter, a stent delivery catheter, an endoscope, a fluid delivery device, other infusion or aspiration devices, delivery (i.e. implantation) devices, and the like. Thus, while the Figures and descriptions above are directed toward a guidewire, in other applications, sizes in terms of diameter, width, and length may vary widely, depending upon the desired properties of a particular device. The scope of the invention is, of course, defined in the language in which the appended claims are expressed.

What is claimed is:

1. A medical guidewire comprising:
   an elongated non-coiled tubular member extending along a longitudinal axis and defining an inner lumen and having an outer surface, the tubular member including a proximal section, a distal section, a proximal end, and a distal end;
   the distal section including a plurality of angled slots defined therein that form a generally spiral shaped pattern about the longitudinal axis, the distal section having an outer diameter;
   wherein the plurality of angled slots are disposed at a non-normal angle relative to the longitudinal axis; and
   the proximal section having an outer diameter that is less than the outer diameter of the distal section;
   wherein the inner lumen is at least partially disposed within each of the proximal and distal sections;
   wherein the elongated non-coiled tubular member includes a distal tip member attached at the distal end such that the inner lumen has a closed distal end.

2. The guidewire of claim 1, wherein the tubular member includes two or more separate tubular components that are attached together to form the tubular member.

3. The guidewire of claim 1, wherein the proximal section is a first discrete tubular component and the distal section is a second discrete tubular component, and the first and second discrete tubular components are attached together to form the tubular member.

4. The guidewire of claim 1, wherein the proximal section and the distal section of the tubular member are of monolithic construction.

5. The guidewire of claim 1, wherein the proximal section includes a plurality of slots defined in at least a portion thereof.

6. The guidewire of claim 5, wherein the plurality of slots defined in the proximal section are disposed at an angle relative to the longitudinal axis that is different from the angle of the slots in the distal section.

7. The guidewire of claim 6, wherein the plurality of slots defined in the proximal section are disposed at an angle that is generally perpendicular to the longitudinal axis.

8. The guidewire of claim 1, wherein at least some of the angled slots are disposed adjacent the distal end of the tubular member.

9. The guidewire of claim 1, wherein each of the slots includes a center line that extends both laterally along and radially about the longitudinal axis such that the slots make less than one full revolution about the longitudinal axis.

10. The guidewire of claim 1, wherein the distal section comprises a first material, and the proximal section comprises a second material different from the first material.

11. The guidewire of claim 1, wherein the distal section and the proximal section are made of the same material.

12. The guidewire of claim 1, wherein the tubular member comprises a metallic material.

13. The guidewire of claim 1, wherein the tubular member comprises a super-elastic material.

14. The guidewire of claim 1, wherein the tubular member comprises a nickel-titanium alloy.

15. The guidewire of claim 1, wherein the tubular member comprises a linear elastic nickel-titanium alloy.

16. The guidewire of claim 1, wherein the tubular member comprises a super-elastic nickel-titanium alloy.

17. The guidewire of claim 1, further including a core wire attached to the tubular member, the core wire including a distal section and a proximal section, wherein at least a portion of the distal section of the core wire is disposed within the lumen of the tubular member.

18. A medical guidewire comprising:
an elongated tubular member extending along a longitudinal axis and defining an inner lumen and having an outer surface, the tubular member including a proximal section, a distal section, a proximal end, and a distal end;
a plurality of first slots defined in at least a portion of the distal section of the tubular member, the first slots being disposed at a non-normal angle relative to the longitudinal axis such that the slots form a generally spiral shaped pattern about the longitudinal axis; and
a plurality of second slots defined in at least a portion of the proximal section of the tubular member that are configured to increase the lateral flexibility of the tubular member, the second slots being disposed at an angle relative to the longitudinal axis that is different from the angle of the first slots;
wherein the elongated tubular member includes a distal tip member attached at the distal end such that the inner lumen has a closed distal end.

19. The guidewire of claim 18, wherein the first slots are disposed at an angle in the range of about 35 to 85 degrees relative to the longitudinal axis.

20. The guidewire of claim 18, wherein the angle of the second slots is generally perpendicular to the longitudinal axis.

21. The guidewire of claim 18, wherein the tubular member includes two or more discrete tubular components that are attached together to form the tubular member.

22. The guidewire of claim 18, wherein the proximal section and the distal section of the tubular member are of monolithic construction.

23. The guidewire of claim 18, wherein the tubular member comprises a metallic material.

24. The guidewire of claim 18, wherein the tubular member comprises a nickel-titanium alloy.

25. The guidewire of claim 18, wherein the tubular member comprises a linear elastic nickel-titanium alloy.

26. The guidewire of claim 18, wherein the distal section has an outer diameter, and the proximal section has an outer diameter that is less than the outer diameter of the distal section.

27. The guidewire of claim 18, further including a core wire attached to the tubular member, the core wire including a distal section and a proximal section, wherein at least a portion of the distal section of the core wire is disposed within the lumen of the tubular member.

28. The guidewire of claim 18, wherein at least some of the first slots are aligned to form a non-continuous spiral groove that extends radially about the outer surface of the distal section of the tubular member.

29. The guidewire of claim 18, wherein each of the first slots includes a center line that extends both laterally along and radially about the longitudinal axis.

30. A guidewire for crossing an occlusion in a vessel lumen of a patient, the guidewire comprising:
an elongated tubular member extending along a longitudinal axis and defining an inner lumen and having an outer surface, the tubular member including a proximal section, a distal section, a proximal end, and a distal end, at least a portion of the tubular member including a plurality of slots defined therein that are configured to increase the lateral flexibility of the tubular member; and
means for engaging the occlusion and pulling at least a portion of the guide wire through the occlusion when a predetermined twisting motion is applied to the guidewire;
wherein the distal section has an outer diameter, and the proximal section has a generally constant outer diameter that is less than the outer diameter of the distal section;
wherein the inner lumen is at least partially disposed within each of the proximal and distal sections;
wherein the elongated tubular member includes a distal tip member attached at the distal end such that the inner lumen has a closed distal end.

* * * * *